US008625869B2

(12) United States Patent
Harder et al.

(10) Patent No.: US 8,625,869 B2
(45) Date of Patent: Jan. 7, 2014

(54) VISUALIZATION OF MEDICAL IMAGE DATA WITH LOCALIZED ENHANCEMENT

(75) Inventors: Martin Harder, Nürnberg (DE); Xiang Sean Zhou, Exton, PA (US)

(73) Assignees: Siemens Medical Solutions USA, Inc., Malvern, PA (US); Siemens Aktiengesellschaft, München (DE)

( * ) Notice: Subject to any disclaimer, the term of this patent is extended or adjusted under 35 U.S.C. 154(b) by 320 days.

(21) Appl. No.: 13/111,376

(22) Filed: May 19, 2011

(65) Prior Publication Data

US 2011/0286630 A1   Nov. 24, 2011

Related U.S. Application Data

(60) Provisional application No. 61/347,064, filed on May 21, 2010.

(51) Int. Cl.
*G06K 9/00* (2006.01)

(52) U.S. Cl.
USPC .......................................................... 382/131

(58) Field of Classification Search
USPC .................. 382/128, 131, 256, 299; 250/583; 378/4, 21
See application file for complete search history.

(56) References Cited

U.S. PATENT DOCUMENTS

| | | | |
|---|---|---|---|
| 5,582,189 A | 12/1996 | Pannozzo | |
| 6,501,826 B1 | 12/2002 | Kropfeld | |
| 8,035,380 B2 * | 10/2011 | Kasugai | 324/309 |
| 8,437,524 B2 * | 5/2013 | Bontus et al. | 382/131 |
| 2002/0054662 A1 * | 5/2002 | Verdonck et al. | 378/62 |
| 2005/0122343 A1 * | 6/2005 | Bailey et al. | 345/619 |
| 2006/0281971 A1 * | 12/2006 | Sauer et al. | 600/109 |
| 2006/0285730 A1 * | 12/2006 | Habets et al. | 382/128 |
| 2007/0237369 A1 * | 10/2007 | Brunner et al. | 382/128 |
| 2008/0118132 A1 * | 5/2008 | Ubelhart et al. | 382/131 |
| 2009/0304593 A1 * | 12/2009 | Frinking et al. | 424/9.1 |
| 2010/0082365 A1 | 4/2010 | Noordvyk | |
| 2010/0086185 A1 * | 4/2010 | Weiss | 382/131 |
| 2010/0135554 A1 * | 6/2010 | Kohlmann et al. | 382/128 |
| 2010/0239140 A1 * | 9/2010 | Ruijters et al. | 382/130 |

(Continued)

FOREIGN PATENT DOCUMENTS

WO     2009/145170 A1    12/2009

OTHER PUBLICATIONS

Hong Shen et al., "Localized Priors for the Precise Segmentation of Individual Vertebras from CT Volume Data", Sep. 6, 2008, Medical Image Computing and Computer-Assisted Intervention a MICCAI 2008 [Lecture Notes in Computer Science], Springer Berlin Heidelberg, Berlin, Heidelberg, pp. 367-375.

(Continued)

*Primary Examiner* — Shervin Nakhjavan
(74) *Attorney, Agent, or Firm* — Peter R. Withstandley

(57) ABSTRACT

Systems and methods for visualization of medical image data with localized enhancement. In one implementation, image data of a structure of interest is resampled within a predetermined plane to generate at least one background image of the structure of interest. In addition, at least one local image is reconstructed to visually enhance at least one local region of interest associated with the structure of interest. The local image and the background image are then combined to generate a composite image.

22 Claims, 11 Drawing Sheets

(56) References Cited

U.S. PATENT DOCUMENTS

2010/0303319 A1* 12/2010 Wang .......................... 382/131
2010/0310036 A1* 12/2010 Burleton et al. ................. 378/5
2011/0102430 A1*  5/2011 Eberhard et al. ............. 345/420

OTHER PUBLICATIONS

International Search Report of Application No. PCT/US2011/037279 dated Aug. 17, 2011.

* cited by examiner

VISUALIZATION OF MEDICAL IMAGE DATA WITH LOCALIZED ENHANCEMENT

CROSS-REFERENCE TO RELATED APPLICATION

The present application claims the benefit of U.S. provisional application No. 61/347,064 filed May 21, 2010, the entire contents of which are herein incorporated by reference.

TECHNICAL FIELD

The present disclosure relates generally to the field of medical imaging. More specifically, the present disclosure relates to systems and methods by which medical image data can be reformatted and presented for facilitating analysis of particular structures within the images.

BACKGROUND

The field of medical imaging has seen significant advances since the time X-ray images were first used to determine anatomical abnormalities. Medical imaging hardware has progressed in the form of newer machines such as medical resonance imaging (MRI) scanners, computed axial tomography (CAT) scanners, etc. Due to the large amount of image data generated by such modern medical scanners, there has been and remains a need for developing image processing techniques that can automate some or all of the processes to determine the presence of anatomical abnormalities in scanned medical images.

One useful image processing technique involves the identification and labeling of specific structures of interest. For example, spine structures are highly ordered, rigid and stable in shape, which make them useful for referencing other anatomies and pathologies. To make full use of the structural advantage of spine structures, they should be extracted and labeled individually.

Spine labeling can be useful in various medical applications. One such application is in diagnostic, therapeutic and spinal anesthesia, which typically involves locating the site for lumbar puncture by using lumbar vertebrae numbers. Spine labeling can also be useful for procedures that rely on the number of ribs for reference and registration. These procedures include, for example, the placement of a needle in the second intercostal space anteriorly during emergency relief of a tension pneumothorax. In such situation, if the patient has a cervical rib, the physician can easily be misled in placing the needle in a location that is higher than necessary in the neck. Visualization of labeled ribs can also be useful for placement of a chest tube to draw a maemothorax or emphysema. If the ribs are misread, the chest tube may be misguided into the pleural space and cause injury to the thoracic or abdominal viscera. This problem is especially prevalent in developing countries, where advanced investigative facilities (e.g., X-ray or CT) are not readily available.

A further application of spine labeling involves bone grafting procedures. Without spine labeling, locating the correct rib can be difficult if there are more than twelve or less than twelve ribs. Spine analysis and labeling may also be particularly useful in locating the kidney using the angle of T12 and L1, especially in view of the difficulty in approaching the kidney during percutaneous renal biopsy and nephrectomy. Spine labeling and analysis can further be employed in surgical procedures that rely on counting the ribs from the sternal angle. Such procedures include draining pneumothorax and emphysema from the chest, which require the location of the actual site of the apex beat and other valuable levels, as well as the pleura. Other uses of spinal column labeling include, for example, forensic and medical legal pathological identifications.

Despite the importance of spine labeling and analysis, results from automatic spine segmentation and labeling techniques are typically not accurate. Labeling becomes even more complicated in atypical cases where the vertebrae (or other spine structures) have unusual characteristics (e.g., number, width, shape, size, etc.). In addition, imperfect image acquisition processes may result in noisy or incomplete scans that compound the difficulties of ascertaining the total number and positions of the vertebrae. Therefore, labels often have to be manually validated and corrected by the radiologist to ensure accuracy. This verification process, however, is extremely time-consuming and error-prone, typically involving repeated scrolling of multiple images to check the rib connections (e.g., lumbarization, sacralization, 11 or 13 T-spine, etc.) and labels of the vertebrae.

Accordingly, there is a need for improved systems and methods to facilitate efficient inspection, labeling, and analysis of the spinal column.

SUMMARY

The present disclosure relates to visualization of medical image data with localized enhancement. In one implementation, image data of a structure of interest is re-sampled within a predetermined plane to generate at least one background image of the structure of interest. In addition, at least one image is reconstructed to visually enhance at least one local region of interest associated with the structure of interest. The local image and the background image are then combined to generate a composite image.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
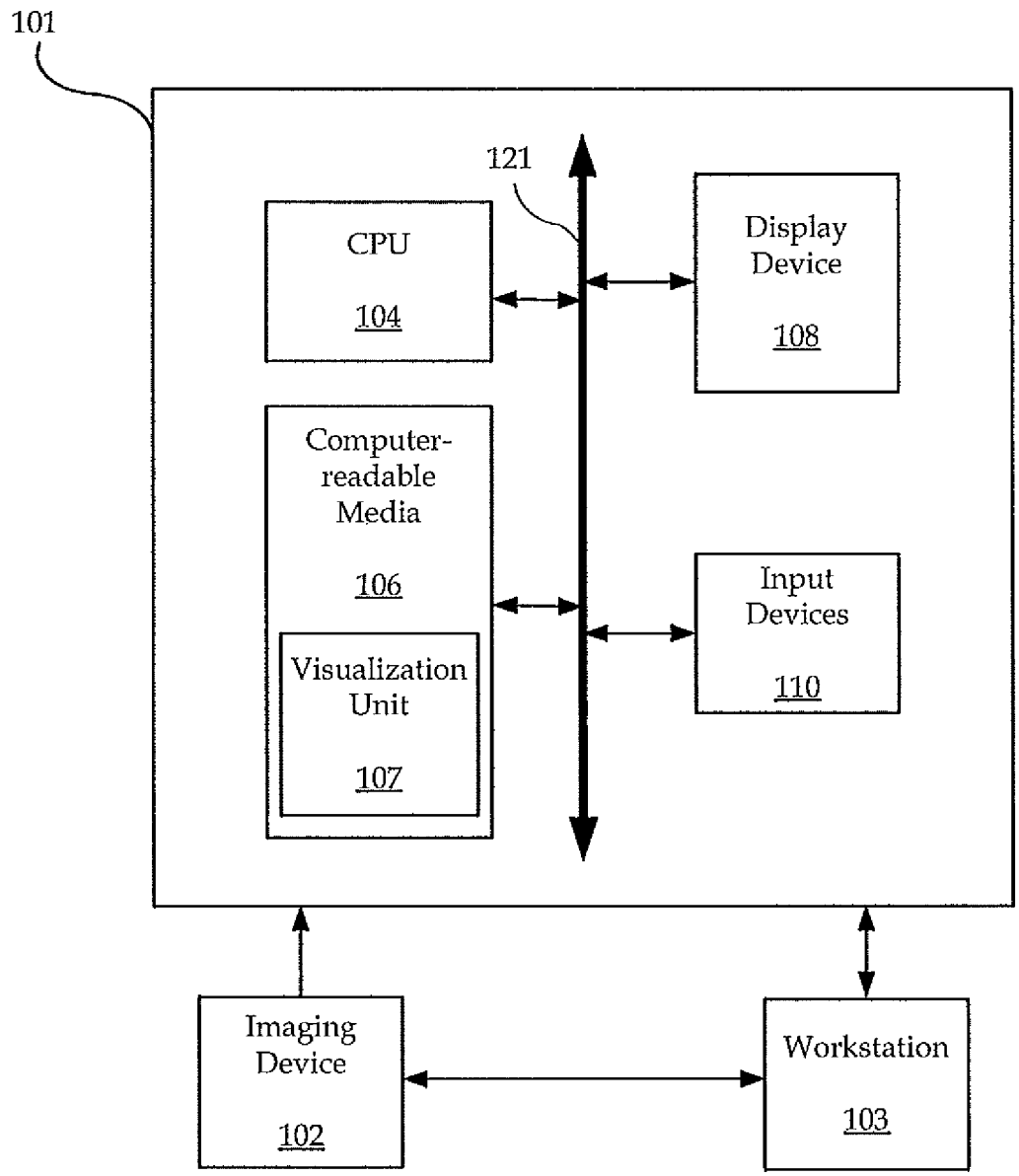
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulate and transform data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

In the following description, for purposes of explanation, specific numbers, materials and configurations are set forth in order to provide a thorough understanding of the present frameworks and methods and in order to meet statutory written description, enablement, and best-mode requirements. However, it will be apparent to one skilled in the art that the present frameworks and methods may be practiced without the specific exemplary details. In other instances, well-known features are omitted or simplified to clarify the description of the exemplary implementations of present frameworks and methods, and to thereby better explain the present frameworks and methods. Furthermore, for ease of understanding, certain method steps are delineated as separate steps; however, these separately delineated steps should not be construed as necessarily order dependent in their performance.

The present technology relates to visualization of medical image data with localized enhancement. In accordance with one implementation, a composite image of a structure of interest (e.g., spinal column) is reconstructed from the original image data set. The composite image includes a local image that visually enhances a localized region of interest, and is combined with a background image that provides contextual information of the structure of interest. The local image may be a maximum or minimum intensity projection image, while the background image may be a multi-planar reconstruction (MPR) image, a curved MPR image, a summation-based, an average-based or a filtering-based projection image. The use of such reconstructed composite images provides, for example, the information necessary for a human user to visually verify labels generated by automated or semi-automated systems. These exemplary advantages and features will be described in more detail in the following description.

It is understood that while a particular application directed to visualizing the spinal column may be shown, the technology is not limited to the specific embodiments illustrated. The present technology has application to, for example, visualizing other types of anatomical structures, such as the aorta, smaller branches near the aorta, blood vessels, airways, brain, colon, etc. In addition, the present framework can be applied to image data acquired by different imaging modalities, including but not limited to, magnetic resonance (MR) imaging, computed tomography (CT), helical CT, x-ray, positron emission tomography (PET), PET-CT, fluoroscopic, ultrasound, single-photon emission computed tomography (SPECT), SPECT-CT, MR-PET, etc.

FIG. 1 is a block diagram illustrating an exemplary system 100. The system 100 includes a computer system 101 for implementing the framework as described herein. The computer system 101 may be further connected to an imaging device 102 and a workstation 103, over a wired or wireless network. The imaging device 102 may be a radiology scanner, such as a magnetic resonance (MR) scanner or a CT scanner, for acquiring image data.

Computer system 101 may be a desktop personal computer, a portable laptop computer, another portable device, a mini-computer, a mainframe computer, a server, a storage system, a dedicated digital appliance, a communication device, or another device having a storage sub-system configured to store a collection of digital data items. In one implementation, computer system 101 comprises a processor or central processing unit (CPU) 104 coupled to one or more non-transitory computer-readable media 106 (e.g., computer storage or memory), display device 108 (e.g., monitor) and various input devices 110 (e.g., mouse or keyboard) via an input-output interface 121. Computer system 101 may further include support circuits such as a cache, power supply, clock circuits and a communications bus. Various other peripheral devices, such as additional data storage devices and printing devices, may be connected to the computer system 101.

The present technology may be implemented in various forms of hardware, software, firmware, special purpose processors, or a combination thereof, either as part of the micro-instruction code or as part of an application program or software product, or a combination thereof, which is executed via the operating system. In one implementation, the techniques described herein are implemented as computer-readable program code tangibly embodied in non-transitory computer-readable media 106. In particular, the present techniques may be implemented by visualization unit 107. Non-transitory computer-readable media 106 may include random access memory (RAM), read only memory (ROM), magnetic floppy disk, flash memory, and other types of memories, or a combination thereof. The computer-readable program code is executed by CPU 104 to process images (e.g., MR or CT images) acquired by, for example, imaging device 102 (e.g., MR or CT scanner). As such, the computer system 101 is a general-purpose computer system that becomes a specific purpose computer system when executing the computer readable program code. The computer-readable program code is not intended to be limited to any particular programming language and implementation thereof. It will be appreciated that a variety of programming languages and coding thereof may be used to implement the teachings of the disclosure contained herein.

The same or different computer readable media 106 may be used for storing the visualization instructions, knowledge base, individual patient data, database of previously treated patients (e.g., training data), and so forth. The patient records, including associated image data, may be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a picture archiving and communication system (PAC), or any other now known or later developed hospital, medical institution, medical office, testing facility, pharmacy or other medical patient record storage system.

The workstation 103 may include a computer and appropriate peripherals, such as a keyboard and display device, and can be operated in conjunction with the entire CAD system 100. For example, the workstation 103 may communicate with the imaging device 102 so that the image data collected by the imaging device 102 can be rendered at the workstation 103 and viewed on a display device. The workstation 103 may include a user interface that allows the radiologist or any other skilled user (e.g., physician, technician, operator, scientist, etc.), to manipulate the image data. Further, the workstation 103 may communicate directly with the computer system 101 to display processed image data and/or output image processing results.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

Figure 2:
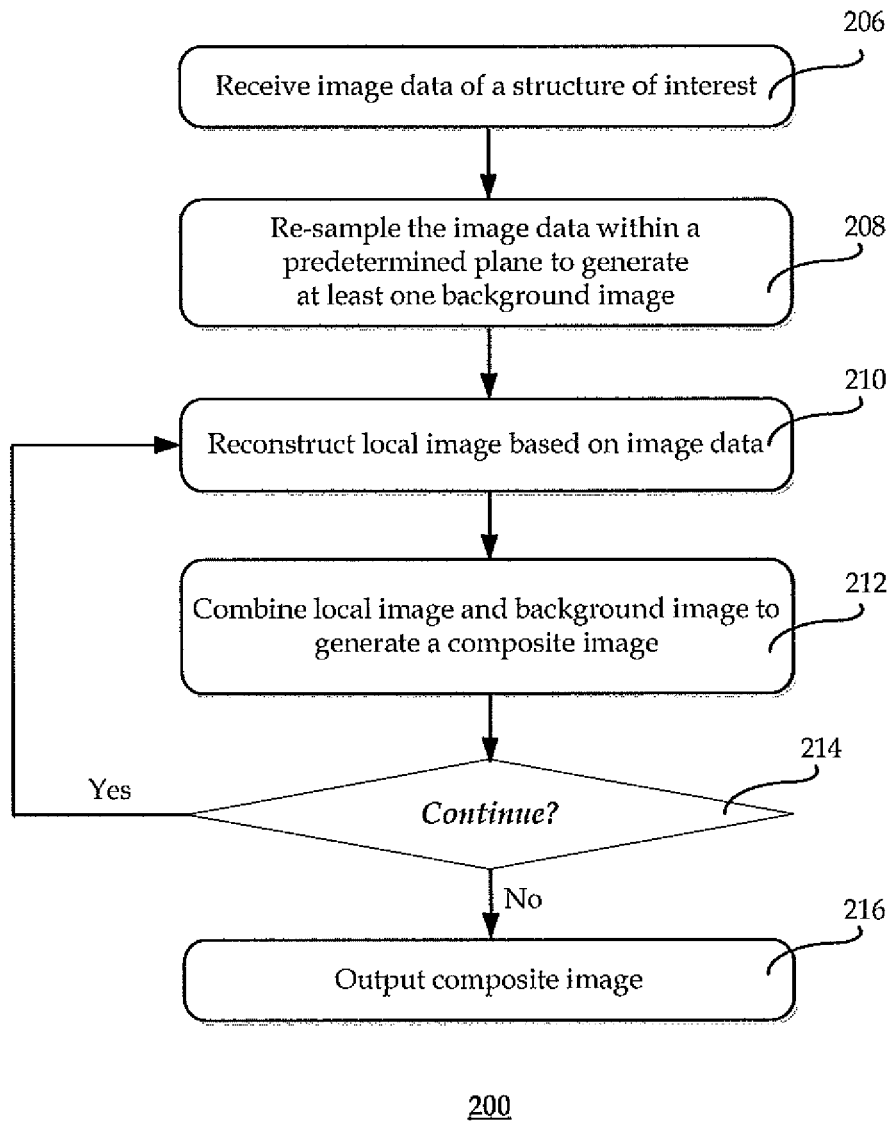
FIG. 2 is a flow-chart illustrating an exemplary method of visualizing a structure of interest.

FIG. 2 shows an exemplary method 200 of visualizing a structure of interest. The steps of the method 200 may be performed in the order shown or a different order. Additional, different, or fewer steps may be provided. Further, the method 200 may be implemented with the system of FIG. 1, a different system or a combination thereof. The same or different systems can perform labeling and visualization of the structure of interest. For example, one computer system may be used for automatically segmenting and labeling the structure of interest, and a different computer system may be used for reconstructing the composite images for visualization.

As shown in FIG. 2, at 206, image data representing a structure of interest is received. The structure of interest is any anatomical structure or portion thereof that has been identified for further study and examination (e.g., a spine, aorta, brain, colon, or any other structure). In one implementation, the image data comprises a volumetric image data set in Digital Imaging and Communications in Medicine (DICOM) format or any other file format. The image data may be received from, for example, a storage device, a database system or an archiving system, such as a picture archiving and communication (PAC) system. In addition, the image data may be acquired by, for example, the imaging device 102 using techniques such as magnetic resonance (MR) imaging, computed tomography (CT), helical CT, x-ray, positron emission tomography (PET), PET-CT, fluoroscopic, ultrasound, single-photon emission computed tomography (SPECT), SPECT-CT, MR-PET, etc.

Optionally, anatomical landmarks of the structure of interest are automatically, semi-automatically or manually detected. For example, an image processing technique may be performed to automatically identify anatomical landmarks of the structure of interest, such as individual vertebrae, certain discs, facet joints or ribs (e.g., first and last ribs) of a spine. The identified landmarks may be marked by a graphical indicator (e.g., dot or cross) and/or text label.

Various types of image processing techniques may be applied to detect the anatomical landmarks, including thresholding, region-growing, segmentation or edge detection algorithms. In one implementation, the image processing technique is a machine learning-based algorithm that trains a discriminative classifier based on a set of training samples. An exemplary machine learning-based algorithm is described in U.S. Pat. No. 7,876,938, the disclosure of which is herein incorporated by reference. Alternatively, or in combination thereof, a user interface may be provided to accept user input identifying one or more points located inside a component (e.g., vertebra) of the structure of interest (e.g, spine). The user-provided points may be used to, for example, seed a region-growing algorithm, adaptive thresholding technique or any other technique that can segment and identify regions around the user-provided points.

Additionally, the orientation of the anatomical landmarks may also be automatically or semi-automatically determined. For example, intervertebral disc orientation may be determined by estimating an orientation field or a centerline from segmented vertebrae regions. It should be understood that other techniques may also be employed.

After identification, the landmarks may be labeled in accordance with a standard naming convention. For example, in the context of labeling the individual vertebrae of a human spine, the standard C1-C7, T1-T12, L1-L5 and S1-S5 naming convention may be followed to label the 7 cervical, 12 thoracic, 5 lumbar and 5 sacral vertebrae respectively. Other types of naming conventions may also be applied. The labels are placed at the appropriate positions within or near the detected landmarks of the structure of interest. The labeling direction may be, for example, in the head-to-feet direction starting at the first thoracic vertebra T1.

Figure 3B:
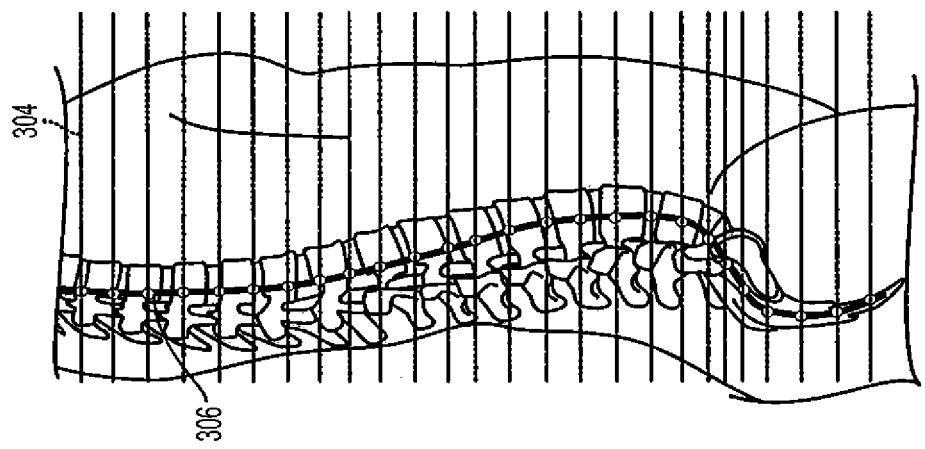
FIGS. 3(a)-(b) illustrate two exemplary methods of re-sampling.
Figure 3A:
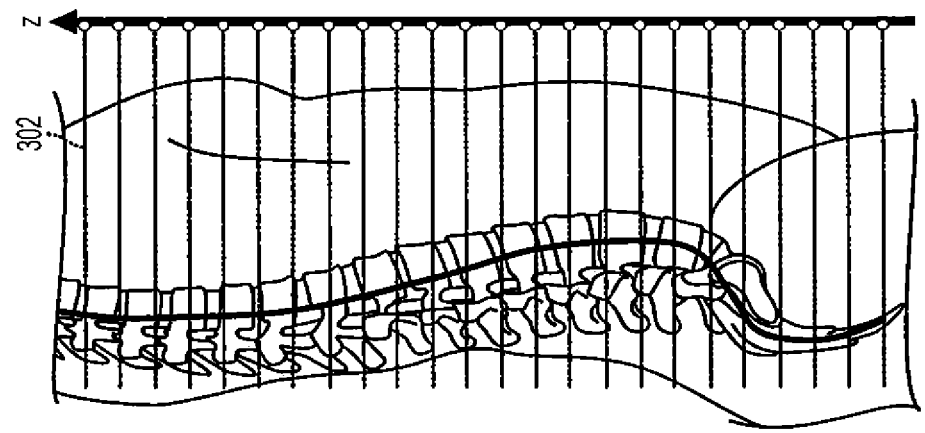

At 208, at least one background image of the structure of interest may be generated by re-sampling the original image data within a predetermined plane. This allows the image data to be viewed in a different plane from which it was acquired. The term "plane" as used herein refers to either a flat or a curved surface. More particularly, the sampling plane may cut through the volume data, and be defined along a straight line or a curved line (e.g., centerline of the structure of interest). The re-sampling may be performed uniformly along a straight or a curved line. For example, FIGS. 3(a)-(b) illustrate two exemplary methods of re-sampling, FIG. 3(a) illustrates uniform sampling along a system coordinate axis Z (or body axis or head-to-feet direction), while FIG. 3(b) illustrates uniform sampling along the centerline 306 of the spine. It should be understood that other types of re-sampling may also be performed.

Figure 4:
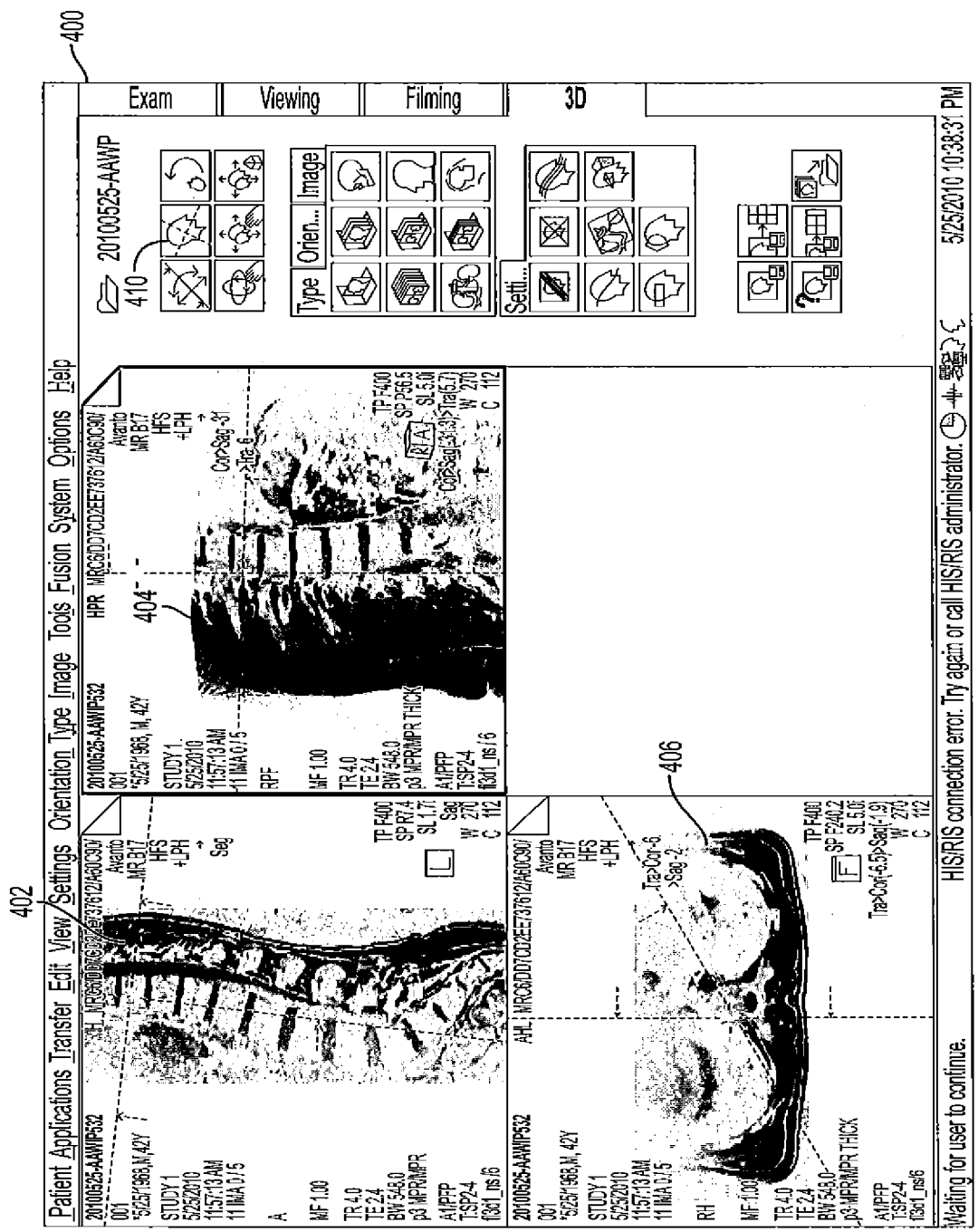
FIG. 4 shows an exemplary graphical user interface.

The sampling plane may be an axial plane that is perpendicular to the body axis of the subject (e.g., patient), a coronal plane that is perpendicular to the axial plane but parallel to the front of the subject's body, a sagittal plane that is perpendicular to both the axial and coronal planes, or an oblique (or non-orthogonal) plane in any other orientation or angle. In one implementation, the coronal plane is defined along the anteroposterior (A-P) median axis. The sagittal plane may be defined along the right-left (R-L) median axis. It is understood that other types of flat or curved sampling planes may also be used. In addition, the position and/or orientation of the re-sampling plane can be automatically or interactively defined by the user. FIG. 4 shows an exemplary graphical user interface 400 that may be used by the user to interactively specify the sampling plane. Three reconstructed background images (402, 404, 406) representing the coronal, sagittal and axial views of the spine are shown. The orientation of the sampling can be specified by selecting the user interface function button 410 and specifying the position and/or angle. Additionally, the user may also manually add new landmarks or edit existing landmarks detected by the algorithm, and/or use them to form a spatial curve (curve in the 3D space), along which the sampling plane will go through.

Figure 5:
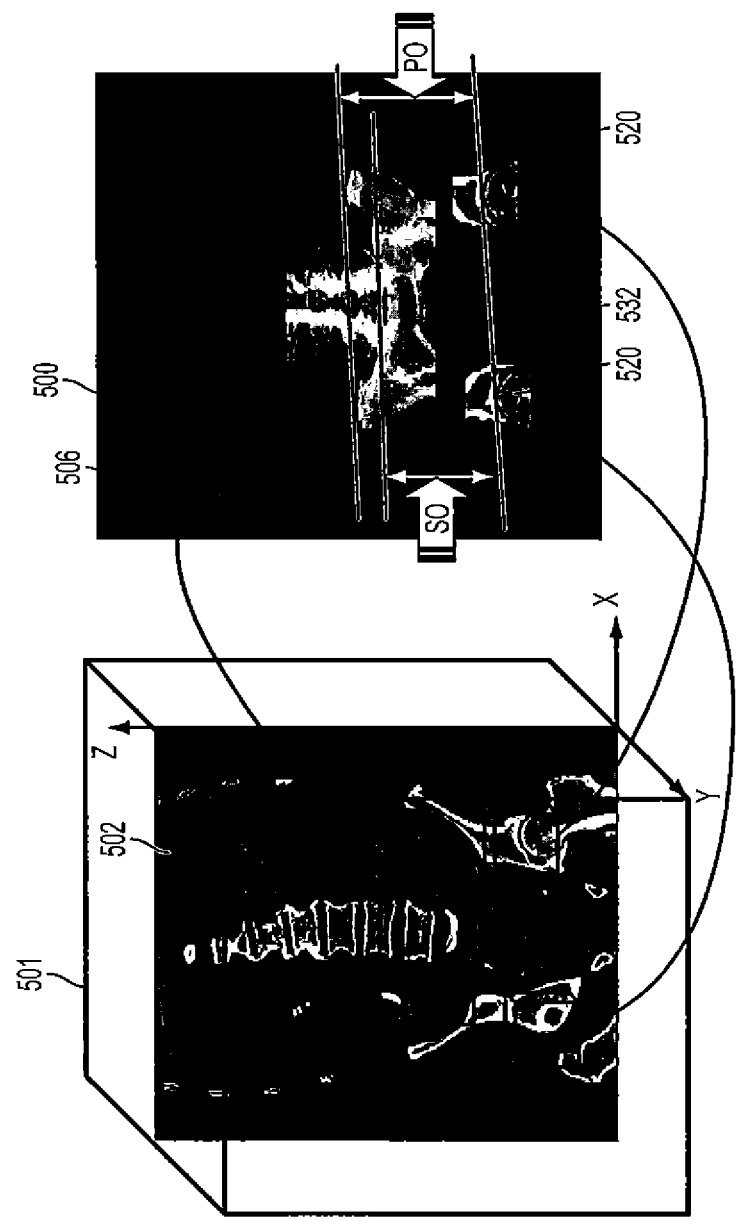
FIG. 5 shows an exemplary average-based background image in a reconstructed composite image.

In one implementation, the reconstructed background image is an average-based projection image. FIG. 5 shows an exemplary average-based projection background image 506 in a composite image 500. The average-based projection background image 506 is reconstructed by averaging the 3D image volume 501 in a front-to-back direction. The exemplary projection image 506 may also be reconstructed by re-sampling the image data in the neighborhood about each sampling point on a flat plane 502 of the volume bounding box 501. The flat plane 502 may be defined by, for example, the local system X and Z axes as shown. In extreme cases involving a very narrow neighborhood comparable to, or smaller than, a voxel dimension, tri-linear interpolation may be performed on the voxel values neighboring the sampling point to obtain an initial value to be associated with the sampling point. To adjust the color and brightness of the pixel in the background image, a transfer function may be applied to this initial value to map the data value to a color, opacity and/or intensity.

Figure 6:
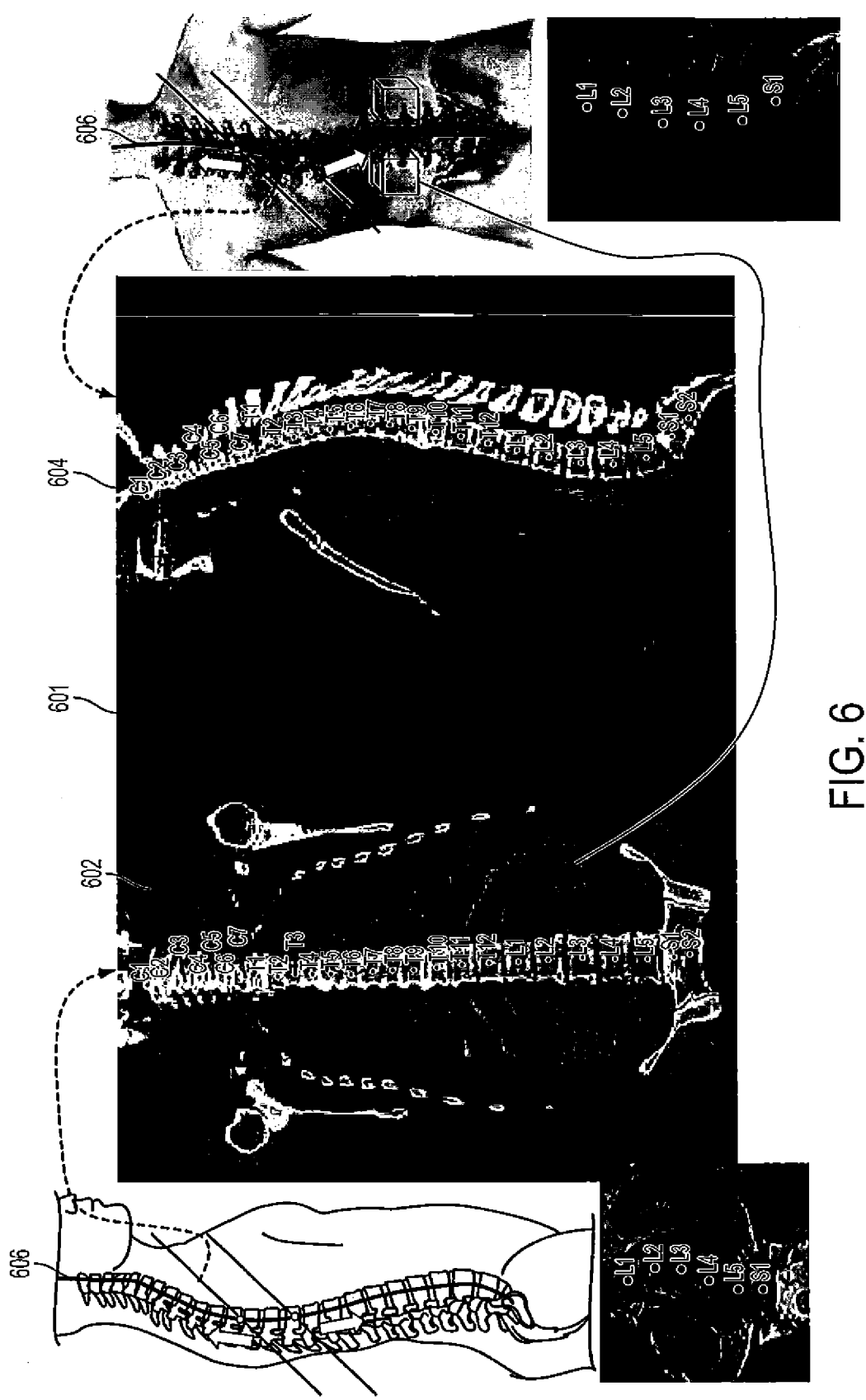
FIG. 6 shows exemplary curved MPR background image segments in a composite image.

In another implementation, the reconstructed background image is a curved MPR image. FIG. 6 shows exemplary curved MPR background image segments 602 and 604 in the composite image 601. Image 602 is a coronal curved MPR image and image 604 is a sagittal curved MPR image of the subject's body. The curved re-sampling plane extends through the voxel data along the general direction of the spine (or its centerline) 606. The centerline or visualization points along the spine may be extracted by, for example, landmark detection techniques or structure segmentation techniques that trace the edge voxels of the structure of interest.

Figure 7:
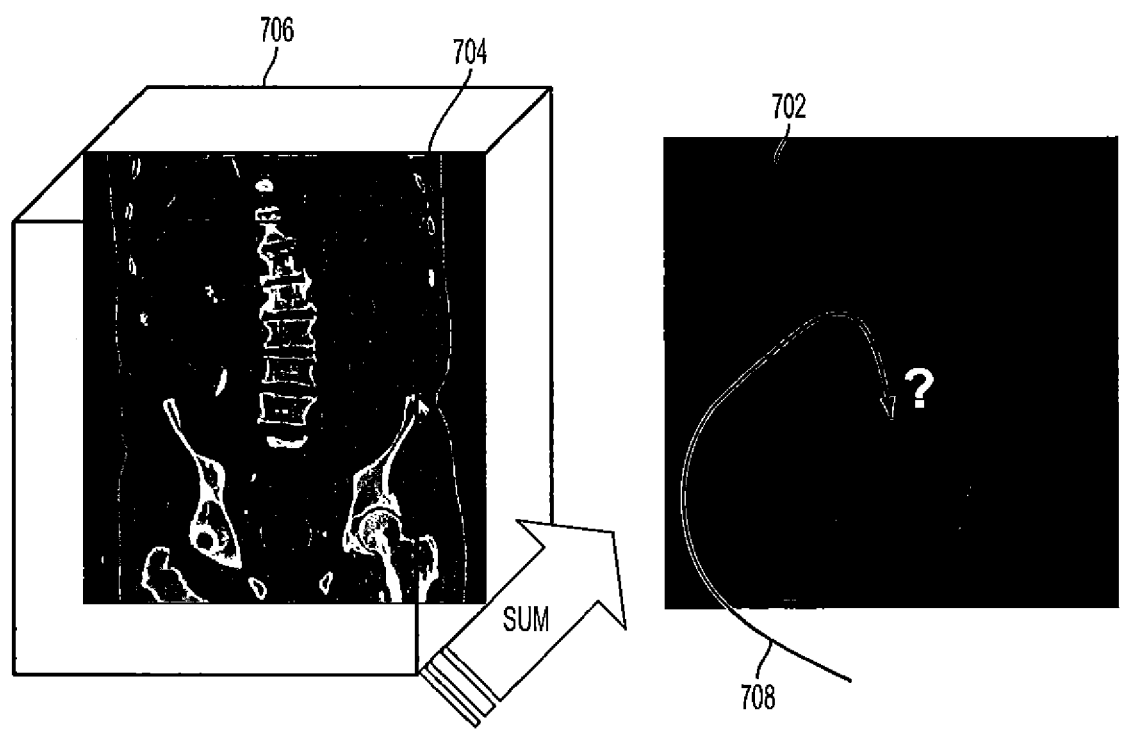
FIG. 7 shows an exemplary summation image.

In yet another implementation, the background image is a summation-based image. Multiple slices of a sub-volume of the original image data set may be combined into the new reformatted background image to form an average or any other function of the image data. Alternatively, or in combination thereof, the reconstructed background image may be a filtering-based image. Various types of image filters, such as a mean or median filter, spatial filter, adaptive filter, Gaussian filter, wavelet transform filter, Fourier transform filter, contourlet transform filter, etc., may be applied to the image data to generate the filtered background image. FIG. 7 shows an exemplary summation image 702. Multiple slices 704 within the sub-volume 706 are combined to form a background image 702. However, although many clinically irrelevant artifacts are diminished or removed, the resulting background image 702 still provides very poor visibility of the vertebra 708 under study. To enhance visualization, a local image may be reconstructed, as will be discussed with reference to step 210.

Figure 8:
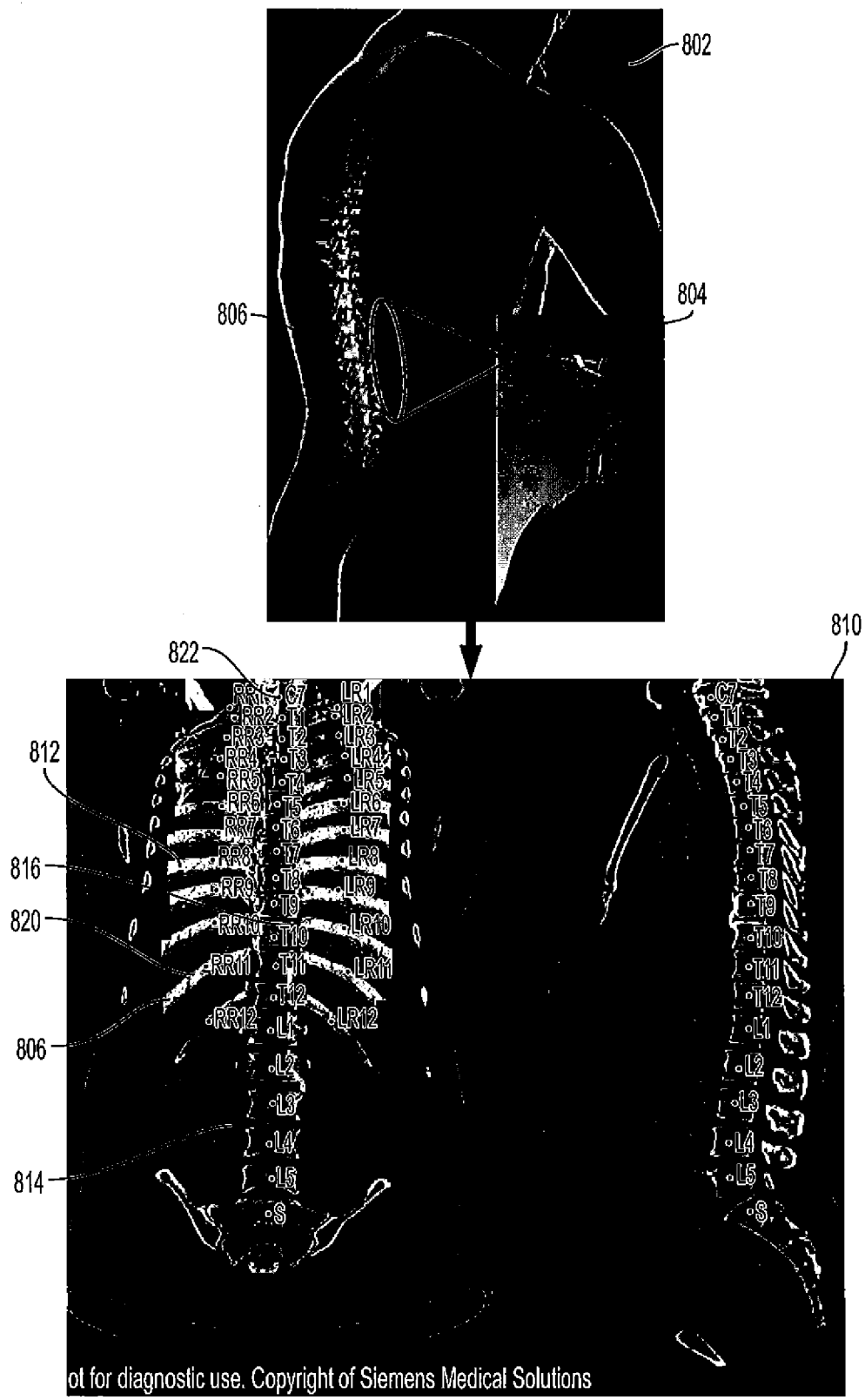
FIG. 8 illustrates the visual effect of presenting a local image.

At 210, a local image is re-constructed based on the original image data set. The local image visually enhances a local region of interest (ROI) associated with the structure of interest. The local ROI is an area of focus represented by a subset of the pixels representing the structure of interest or portion thereof. For example, in the context of spine visualization, the ROI may be a vertebral connection. FIG. 8 illustrates the visual effect of presenting a local image. As illustrated by image 802, the visual effect is similar to one looking through a virtual endoscope 804 inserted into the body and focusing on a local ROI 806. The reconstructed composite image 810 shows the local image 812 being confined to a local ROI 806 where the ribs connect to the vertebra, so as to minimize distractions from the patient table or other anatomical structures 814 (e.g., other bone structures or organs). The local image 812 provides an intuitive and clear visualization of, for example, one or more vertebra-and-rib connections to enable efficient validation of machine-generated labels 816, as will be described in more detail later.

In one implementation, the position of the local ROI is defined automatically. For example, the local ROI may be automatically defined around a feature point detected by a segmentation technique. Alternatively, a user may define the local ROI interactively. For example, a graphical user interface may be provided to enable the user to select one or more feature points or to define ROI in an image. The two-dimensional shape of the local ROI may be square, rectangular, circular, or any other shape.

In one implementation, visual enhancement of the local ROI is achieved by performing a maximum (or minimum) intensity projection (MIP) technique to reconstruct the local image. The MIP technique is a volume visualization method that involves processing the volumetric image data to reconstruct a two-dimensional (2D) slice that may be perceived as three-dimensional (3D). This may be achieved by projecting in the visualization plane the image data voxels with the maximum (or minimum) voxel intensities that fall in the way of parallel rays traced from the viewpoint to the plane of projection. Referring to FIG. 8, for example, the exemplary local image 812 is reconstructed using maximum intensity projection in the local neighborhood of the spinal column. Since bone typically exhibits a high value in CT image data, the ribs 820 and spine 822 appear prominent because the bone intensity values are selected from the voxels encountered by a given projection ray. Other types of visual enhancement techniques, such as volume rendering technique (VRT), thick MPR, or average projection, may also be employed in either a local or global neighborhood.

A user interface may be provided to allow the user to select the visual enhancement technique for reconstructing the local image. For example, if the user wants to emphasize high density objects (e.g., bone), the user may select maximum intensity projection. Alternatively, minimum intensity projection can be selected if the user wishes to minimize undesirable high intensity artifacts introduced during the imaging acquisition process.

At 212, the reconstructed local and background images are combined to generate a composite image. The background image may serve to provide the contextual information or global overview of the structure of interest, while the local image serves to enhance the visualization of a local ROI associated with the structure of interest. For example, the background image may provide the contextual information for verifying the labels of a spine. The contextual information may include, for instance, display of neighboring vertebrae (e.g., upper and/or lower end of the spine) or surrounding anatomical features (e.g., ribs, sacrum, organs, etc.). More than one background image (e.g., coronal and sagittal images) may be provided in the composite image. Similarly, more than one local image may be provided in the composite image to visually enhance, for example, different local ROIs associated with the structure of interest.

Various layouts of the local and background images in the composite image may be implemented. The ROI in the local image may be aligned with the corresponding ROI in the background image. The positions of the local images and/or background images may also vary, depending on the user preference. In one implementation, at least a portion of the local image overlaps the one or more background images. The overlapping portion may be blended to improve visualization. For example, each pixel of the overlapping portion may be generated as a function of the pixel intensity of the background image and the local image. In some implementations, the local image may appear opaque (or non-transparent) in the overlapping section. A user interface may be provided to allow the user to select the type of blending method used to blend the pixels of the background and local images in the overlap portion. In addition, the user may choose to magnify the local image and select the desired zoom factor, or to select any other type of visual enhancement effects (e.g., color inversion, image refinement, etc.).

Figure 9A:
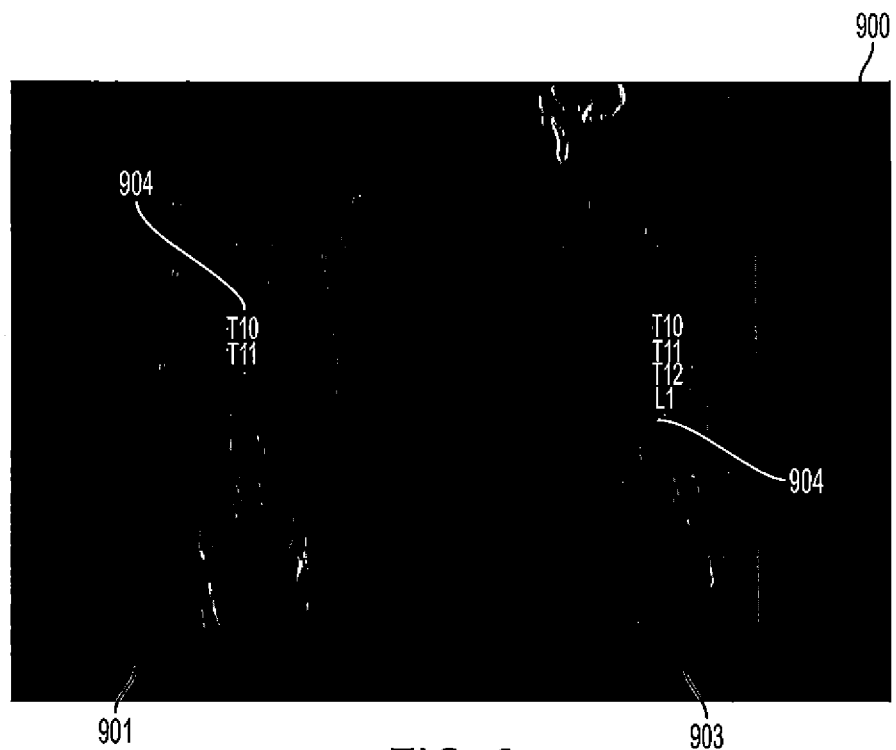
FIGS. 9a-b show a conventional 3D image and an exemplary composite image generated by the present framework respectively.
Figure 9B:
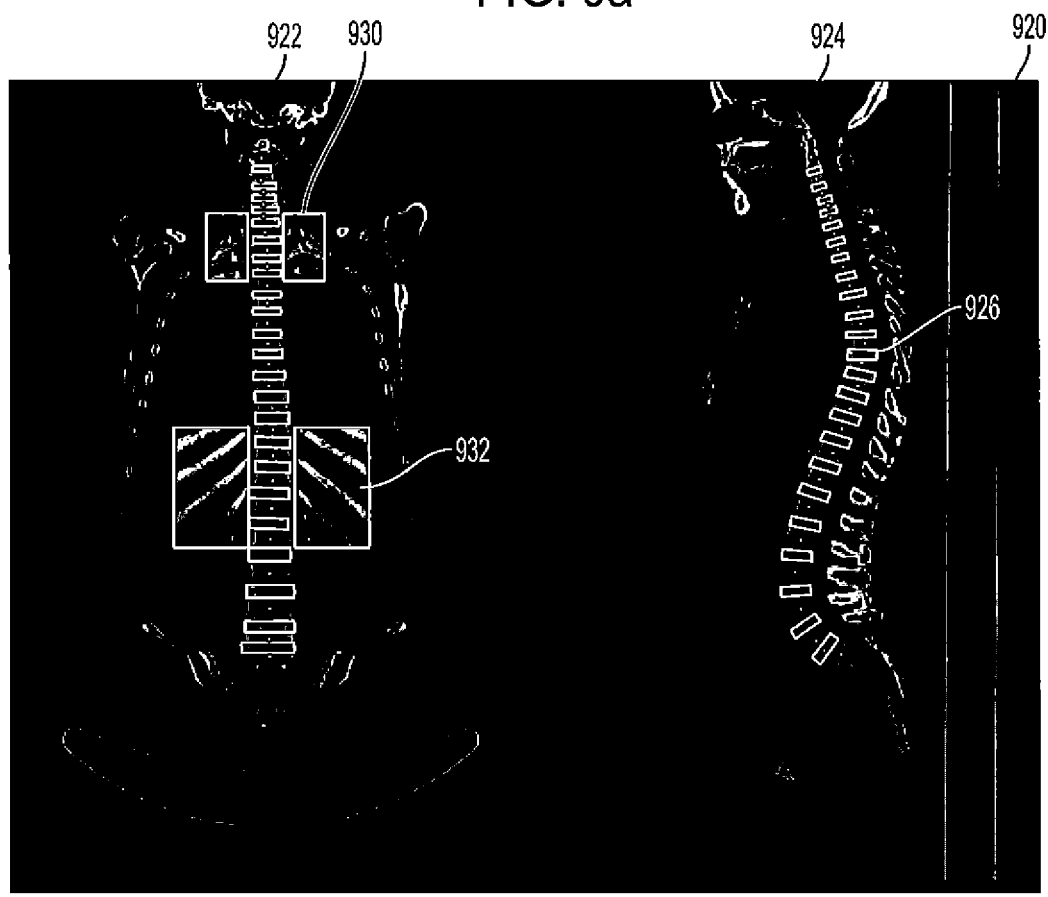

FIGS. 9a-b show a conventional 3D image 900 and an exemplary composite image 920 generated by the present framework respectively. The conventional 3D image 900 presents a coronal view 901 and a sagittal view 903 of the subject's body, including the spine and corresponding labels 904 of the vertebrae. As can be observed, it is difficult to verify the accuracy of the labels 904 because the vertebral connections are almost indistinguishable in the conventional 3D image 900. In comparison, the vertebral connections are highly prominent in the exemplary composite image 920. The composite image 920 includes two background images (922 and 924) presenting coronal and sagittal views. The local images (930 and 932) are overlaid on the background images (922 and 924). The local images (930 and 932) serve to visually enhance the regions of interest including the connections between the ribs and vertebrae, while the background images (922 and 924) serve to provide the contextual information (e.g., upper and/or lower end of the spine, ribs, sacrum, organs, etc.). By visually enhancing the rib-vertebrae connections in their contextual environment, the composite image 920 provides an efficient means for the user to verify and correct the machine-generated labels 926 to ensure their accuracy.

Figure 10:
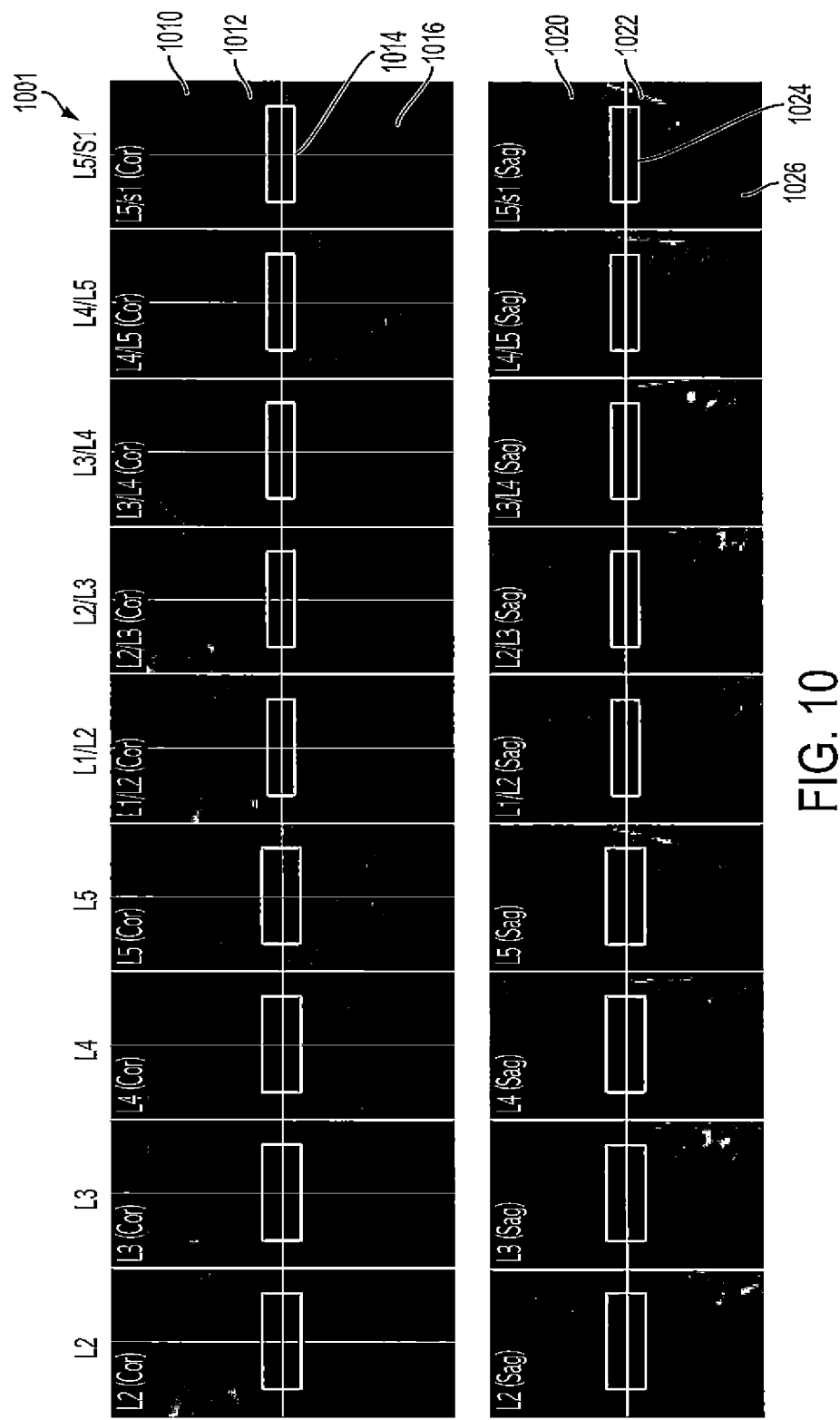
FIG. 10 shows a series of exemplary re-oriented composite images.

In one implementation, the composite image is re-oriented to align the local image at a predetermined location and orientation so as to provide visual consistency. FIG. 10 shows a series of exemplary re-oriented composite images 1001. The top row 1010 shows a set of coronal images while the bottom row shows a corresponding set of sagittal images 1020. The labels (e.g., L2, L3, L4, etc.) indicate the names of the vertebrae captured in the local images (1014 and 1024). It can be observed that each composite image may be re-oriented such that the local image (1014 and 1024) is centralized. To perform the re-orientation, the position of the local image (1014 and 1024) may first be determined. The background images (1016 and 1026) are then reconstructed and re-oriented based on the relative location and orientation of the local image (1014 and 1024).

At 214, the process 200 determines if it should continue reconstructing another local image. For example, the system 101 may prompt the user with, for example, a pop-up text message to query the user for input. The user may be given the option to choose another location on the structure of interest for reconstructing the local image. Once the user is satisfied, the system may proceed to display the resulting composite image.

At 216, the composite image is output by the system 101. The composite image may be saved for quick viewing at a later time. Alternatively or in combination thereof, the composite image may be rendered and displayed immediately on, for example, display device 108 or workstation 103. The composite image may be viewed by a user to verify, for example, the accuracy of machine-generated labels of the structure of interest. For example, the user may inspect the visually enhanced rib-vertebra connections emphasized in the local images to determine if the vertebrae are labeled correctly, while relying on the background images to provide the necessary contextual information for facilitating such verification, as previously described with reference to FIG. 9. By providing both the visually enhanced and contextual information in a single composite image, the present framework advantageously provides an intuitive means to improve the efficiency and accuracy of visual inspection.

In addition to viewing, the composite image may be used for computer-aided detection (CAD) methods (e.g., segmentation) or other image processing methods. For example, a CAD technique may be performed to detect certain landmarks in the reconstructed composite image. The landmarks may also be manually detected by the user via, for example, a graphical user interface. The local image within the composite image enhances such landmarks such that they are more easily detected by the CAD technique or visual inspection.

In one implementation, the spatial relationship between the landmarks in the composite image may be automatically determined. For example, the angular deviation between lines defined by pairs of detected landmarks may be automatically computed. For example, in studies of the human spine, the sacral obliquity (SO), pelvic obliquity (PO), or any other anatomic parameter, may be determined. Such parameters may be particularly useful for diagnosing and treating anomalies or deformities in the skeletal structure. It is understood that other types of parameters, such as the Cobb angle, may also be derived from the landmarks in the composite image.

Figure 11:
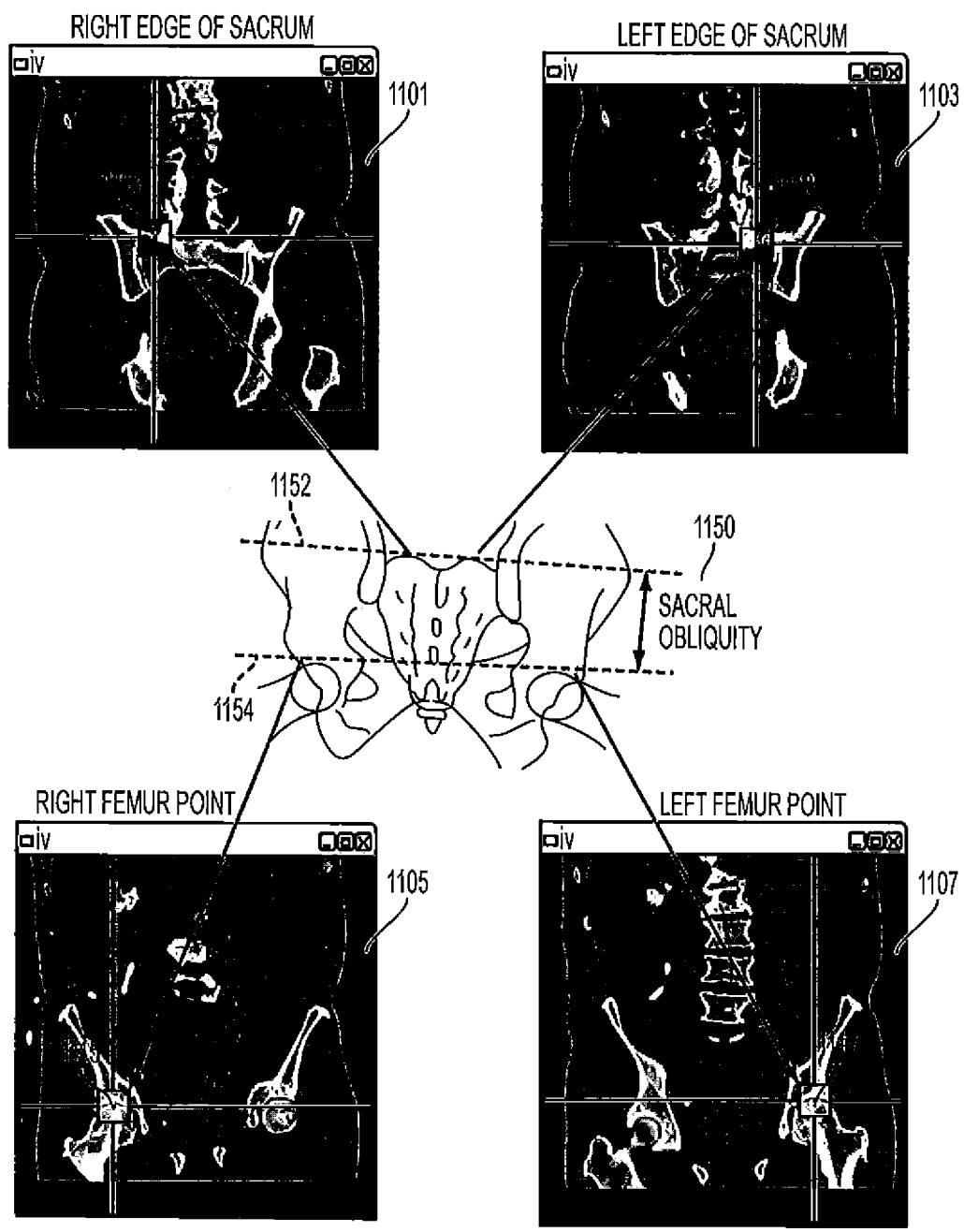
FIG. 11 illustrates the determination of sacral obliquity using conventional images.

FIG. 11 illustrates the determination of sacral obliquity (SO) using conventional 3D CT images (1101, 1103, 1105, 1107). Sacral obliquity (or tilt) refers to the angular deviation of the sacrum 1152 from the horizontal line drawn parallel to a line 1154 across the femoral heads in an axial view 1150 of the sacrum. The sacral line 1152 is defined by the right and left edge points (1111 and 1113) of the sacrum, while the femoral line 1154 is defined by the right and left femur points (1115 and 1117). The measurement points (1111, 1113, 1115, 1117) are typically not found on the same plane. To measure the sacral obliquity, many CT slices (1101, 1103, 1105, 1107) have to be examined to detect and align the measurement points (1111, 1113, 1115, 1117). This process can be very tedious and inefficient.

The present framework advantageously facilitates the determination of SO, PO and other measurements by providing the measurement points in the same composite image. For example, FIG. 5 shows an exemplary composite image 500 reconstructed by the present framework. The composite image 500 presents clinically relevant anatomical features, including relevant measurement points, using local images 520. The sacral line 534 and femoral line 532 are defined by measurement points detected in the same composite image 500. Once these lines are determined, the sacral obliquity (SO) can automatically be computed. Similarly, the pelvic obliquity (PO) may be computed based on the pelvic line 530 and femoral line 532 defined by measurement points detected in the same composite image 500, thereby eliminating the need to scroll through a series of images in search of measurement points.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

Further, although method or process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

The invention claimed is:

1. A system for visualizing medical image data, comprising:
 a memory device for storing non-transitory computer readable program code; and
 a processor in communication with the memory device, the processor being operative with the computer readable program code to:
  (i) receive image data of a structure of interest;
  (ii) resample the image data within a predetermined plane to generate at least one background image of the structure of interest;
  (iii) reconstruct, based on the image data, at least one local image that visually enhances at least one local region of interest associated with the structure of interest; and
  (iv) combine the local image and the background image to generate a composite image with the local image overlaid on the background image.

2. The system of claim 1 wherein the image data comprises magnetic resonance (MR) images, computed tomography (CT) images, helical CT images, x-ray images, positron emission tomography (PET) images, PET-CT images, fluoroscopic images, ultrasound images, single-photon emission computed tomography (SPECT) images, SPECT-CT images or MR-PET images.

3. The system of claim 1 wherein the structure of interest comprises a spine and the local region of interest comprises a vertebral connection.

4. The system of claim 1 wherein the processor is further operative with the computer readable program code to detect one or more anatomical landmarks in the image data.

5. The system of claim 4 wherein the processor is further operative with the computer readable program code to label the one or more detected anatomical landmarks.

6. The system of claim 1 wherein the processor is further operative with the computer readable program code to resample the image data uniformly along a system coordinate axis.

7. The system of claim 1 wherein the processor is further operative with the computer readable program code to resample the image data uniformly along a centerline of the structure of interest.

8. The system of claim 1 wherein the predetermined plane comprises a coronal plane, a sagittal plane or an oblique plane.

9. The system of claim 1 wherein the background image comprises a multi-planar reconstruction image.

10. The system of claim 1 wherein the background image comprises a curved multi-planar reconstruction image.

11. The system of claim 1 wherein the background image comprises a summation-based, an average-based or a filtering-based projection image.

12. The system of claim 1 wherein the processor is further operative with the computer readable program code to generate multiple background images.

13. The system of claim 12 wherein the multiple background images comprise at least one coronal image and at least one sagittal image.

14. The system of claim 1 wherein the local image comprises a maximum intensity projection image or a minimum intensity projection image.

15. The system of claim 1 wherein the processor is further operative with the computer readable program code to reconstruct multiple local images.

16. The system of claim 1 wherein the processor is further operative with the computer readable program code to blend pixels of the background image and the local image in an overlapping portion of the composite image where the background image and the local image overlap, wherein each pixel of the overlapping portion is generated as a function of pixel intensities of the background image and the local image.

17. The system of claim 1 wherein the processor is further operative with the computer readable program code to perform a computer-aided detection method to detect one or more landmarks in the composite image.

18. The system of claim 1 wherein the processor is further operative with the computer readable program code to determine a spatial relationship between landmarks in the composite image.

19. The system of claim 18 wherein the spatial relationship comprises an angular deviation between lines defined by pairs of the landmarks.

20. The system of claim 19 wherein the angular deviation comprises sacral obliquity or pelvic obliquity.

21. A non-transitory computer readable medium embodying a program of instructions executable by machine to perform steps for visualization of image data, the steps comprising:
 (i) receiving image data of a structure of interest;
 (ii) resampling the image data within a predetermined plane to generate at least one background image of the structure of interest;
 (iii) reconstructing, based on the image data, at least one local image that visually enhances at least one local region of interest associated with the structure of interest; and
 (iv) combining the local image and the background image to generate a composite image with the local image overlaid on the background image.

22. A method of visualizing medical image data using a computer system, the method comprising:
 (i) receiving image data of a structure of interest;
 (ii) resampling the image data within a predetermined plane to generate at least one background image of the structure of interest;
 (iii) reconstructing, based on the image data, at least one local image that visually enhances at least one local region of interest associated with the structure of interest; and
 (iv) combining the local image and the background image to generate a composite image with the local image overlaid on the background image.

* * * * *